(12) United States Patent
Sharma et al.

(10) Patent No.: US 12,079,841 B2
(45) Date of Patent: *Sep. 3, 2024

(54) CONFIGURABLE RELEVANCE SERVICE PLATFORM INCORPORATING A RELEVANCE TEST DRIVER

(71) Applicant: Bytedance Inc., Wilmington, DE (US)

(72) Inventors: Kannan Nitin Sharma, San Mateo, CA (US); Srinivasa Vedanarayanan, Sunnyvale, CA (US); Vidhyaa Muralidharan, Sunnyvale, CA (US)

(73) Assignee: Bytedance Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/814,069

(22) Filed: Jul. 21, 2022

(65) Prior Publication Data

US 2023/0052849 A1 Feb. 16, 2023

Related U.S. Application Data

(63) Continuation of application No. 16/895,317, filed on Jun. 8, 2020, now Pat. No. 11,430,013, which is a
(Continued)

(51) Int. Cl.
| | |
|---|---|
| *G06Q 30/02* | (2023.01) |
| *G06F 11/36* | (2006.01) |
| *G06F 17/16* | (2006.01) |
| *G06F 18/22* | (2023.01) |
| *G06F 40/157* | (2020.01) |
| *G06N 20/00* | (2019.01) |
| *G06Q 30/0251* | (2023.01) |
| *G16H 10/60* | (2018.01) |
| *G06Q 30/0242* | (2023.01) |

(52) U.S. Cl.
CPC ..... *G06Q 30/0269* (2013.01); *G06F 11/3688* (2013.01); *G06F 17/16* (2013.01); *G06F 18/22* (2023.01); *G06F 40/157* (2020.01); *G06N 20/00* (2019.01); *G06Q 30/0256* (2013.01); *G16H 10/60* (2018.01); *G06Q 30/0242* (2013.01)

(58) Field of Classification Search
None
See application file for complete search history.

(56) References Cited

U.S. PATENT DOCUMENTS

| | | |
|---|---|---|
| 6,427,132 B1 | 7/2002 | Bowman-Amuah |
| 8,423,408 B1 | 4/2013 | Barnes et al. |
| | (Continued) | |

OTHER PUBLICATIONS

U.S. Appl. No. 13/829,581, filed Mar. 14, 2013, In re: Aggarwal entitled Promotion Offering System, 71 pages.
(Continued)

*Primary Examiner* — Vincent M Cao
(74) *Attorney, Agent, or Firm* — ALSTON & BIRD LLP

(57) ABSTRACT

In general, embodiments of the present disclosure provide for a configurable relevance service platform via a relevance test driver. In embodiments, test configuration data associated with at least one test scenario for a relevance service is received via at least one relevance test driver that interfaces with a relevance test service. Additionally, one or more promotions relevant to a user identifier are determined based at least in part on the test configuration data, and output data associated with the one or more promotions is transmitted to the relevance test service.

20 Claims, 14 Drawing Sheets

Related U.S. Application Data continuation of application No. 15/957,188, filed on Apr. 19, 2018, now Pat. No. 10,713,690, which is a continuation of application No. 13/918,650, filed on Jun. 14, 2013, now Pat. No. 9,978,084.

(56)  References Cited

U.S. PATENT DOCUMENTS

| | | |
|---|---|---|
| 2002/0035568 A1 | 3/2002 | Benthin et al. |
| 2003/0033190 A1 | 2/2003 | Shan et al. |
| 2003/0041050 A1 | 2/2003 | Smith et al. |
| 2005/0166094 A1 | 7/2005 | Blackwell et al. |
| 2005/0189415 A1 | 9/2005 | Fano et al. |
| 2005/0289000 A1 | 12/2005 | Chiang et al. |
| 2008/0011842 A1 | 1/2008 | Curry et al. |
| 2008/0109285 A1 | 5/2008 | Reuther et al. |
| 2008/0162202 A1 | 7/2008 | Khanna et al. |
| 2008/0282231 A1 | 11/2008 | R et al. |
| 2008/0320071 A1 | 12/2008 | Hoskins et al. |
| 2009/0132378 A1 | 5/2009 | Othmer et al. |
| 2009/0327055 A1 | 12/2009 | Kosuru |
| 2010/0191598 A1 | 7/2010 | Toennis et al. |
| 2010/0258621 A1 | 10/2010 | Schlabach et al. |

OTHER PUBLICATIONS

U.S. Appl. No. 16/895,317, filed Jun. 8, 2020, U.S. Pat. No. 11,430,012, Issued.

U.S. Appl. No. 15/957,188, filed Apr. 19, 2018, U.S. Pat. No. 10,713,690, Issued.

U.S. Appl. No. 13/918,650, filed Jun. 14, 2013, U.S. Pat. No. 9,978,084, Issued.

Example Test Configuration

200

▼ checkDDOForDealbankContextScenarios
230 — dealinput_service.json
description.txt
240 — testDefaultContext_output_service.json
210 — testDefaultContext_params_service.json
220 — userinput_service.json

FIG. 2

Example Request Parameters

```
@testDefaultContext_params_service.json ×
[{"email_address":"scenario1.user@groupon.com","division":"san-francisco","date":"2012-04-25",
"delta":"1",
"context":"default",
"max_deal_bank_deals"::2,
"exclude_ranking_groups":[ "noSmartDeals", "noSmartDealsAir", "noFreshnessHoldout" ]}]
```

Example Expected Output

```
@testDefaultContext_output_service.json ×
{"goals": [
  {"permalink": "awesome1-deal",
   "locations": [],
   "dealCategory": null
  }
 ],
 "userKey": null,
 "context": "default",
 "treatment": "71a05f4a0c2105370b8c2ac402a30a32"
}
```

Example Promotion Model Data
(Including Performance Data)

FIG. 11

Example Promotion Model Data
(Including Mock Search Input Data)

```
{
  "id":3031547,
  "uuid":null,
  "type":"deal",
  "permaLink":"some-com1_deatnm-deal",
  "location":[
    {
      "geoPoint":"37.775200,-122.418000",
      "zipCode":null,
      "type":"ACTUAL",
      "id":3145137
    }
  ],
  "en_us_dealTitle":null,
  "en_us_dealSubtitle":null,
  "en_us_dealBriefSummary":null,
  "en_us_dealWriteup":null,
  "en_us_merchantName":null,
  "en_us_merchantWriteup":null,
  "merchantServiceUuid":"c2a97b1-1cce-40bb-8847-0871aed2f135",
  "merchantServiceName":"House / Room",
  "v1CategoryName":"Service",
  "v1SubcategoryName":"House Cleaning",
  "v2CategoryName":"Services",
  "v2SubcategoryName":"Cleaning",
  "v2Subcategory2Name":"House Cleaning",
  "customerTaxonomyCategoryUuid":"e762183-21e7-4c2c-97fc-ec8b7173881c",
  "customerTaxonomyCategoryPermaLink":"home-and-auto",
}
```

“CONFIGURABLE RELEVANCE SERVICE
PLATFORM INCORPORATING A
RELEVANCE TEST DRIVER”

CROSS REFERENCE TO RELATED
APPLICATIONS

This application is a continuation of and claims priority to U.S. patent application Ser. No. 16/895,317, titled "CONFIGURABLE RELEVANCE SERVICE TEST PLATFORM," and filed Jun. 8, 2020, which is a continuation of and claims priority to U.S. patent application Ser. No. 15/957,188, titled "CONFIGURABLE RELEVANCE SERVICE TEST PLATFORM," and filed Apr. 19, 2018, which is a continuation of and claims priority to U.S. application Ser. No. 13/918,650, titled "CONFIGURABLE RELEVANCE SERVICE TEST PLATFORM," and filed Jun. 14, 2013, the contents of which are hereby incorporated herein by reference in their entirety.

FIELD OF THE INVENTION

Embodiments of the invention relate, generally, to a configurable test environment providing verification and validation of a relevance service.

BACKGROUND

A relevance service includes systems and methods that are configured to identify a group of available promotions that are relevant to a user in response to receiving a relevance service request on behalf of that user. A relevance service may determine relevance of a promotion to a user by matching attributes of the promotion to attributes of the user (e.g., user interests, user location, user gender, and/or user purchase behavior).

A promotion provider is an example of a business that relies on effective and timely communication to consumers about promotions that are available for purchase. The likelihood is increased that a particular consumer will proceed to purchase a promotion after receiving notification of available promotions if the provider has the capability to identify a subset of available promotions that are most relevant to the particular consumer and feature those promotions in the notification. Since communicating effectively with a consumer impacts the success of a promotion provider's business, it is important to be able to ensure the consistency and accuracy of the system that performs identification of promotions that are most relevant to the consumer.

Current methods for verification and validation of a relevance service exhibit a plurality of problems that make current systems insufficient, ineffective and/or the like. Through applied effort, ingenuity, and innovation, solutions to improve such methods have been realized and are described in connection with embodiments of the present invention.

SUMMARY

In general, embodiments of the present invention provide herein systems, methods and computer readable media for a configurable test environment within which a relevance service can be invoked to execute one or a combination of test scenarios, each test scenario respectively being configured to exercise one or a combination of features of the relevance service. In embodiments, a test scenario may be configured to use test data that can be simulated and/or be derived from one or a combination of user models and promotion models, and/or be based on aggregated data that has been collected from previous production runs of the relevance service. In embodiments, each test scenario is described as a set of test configuration data. In some embodiments, the test configuration data are represented in a data interchange format that is both human and machine-readable, e.g., JavaScript Object Notation (JSON).

BRIEF DESCRIPTION OF THE DRAWINGS

Figure 1:
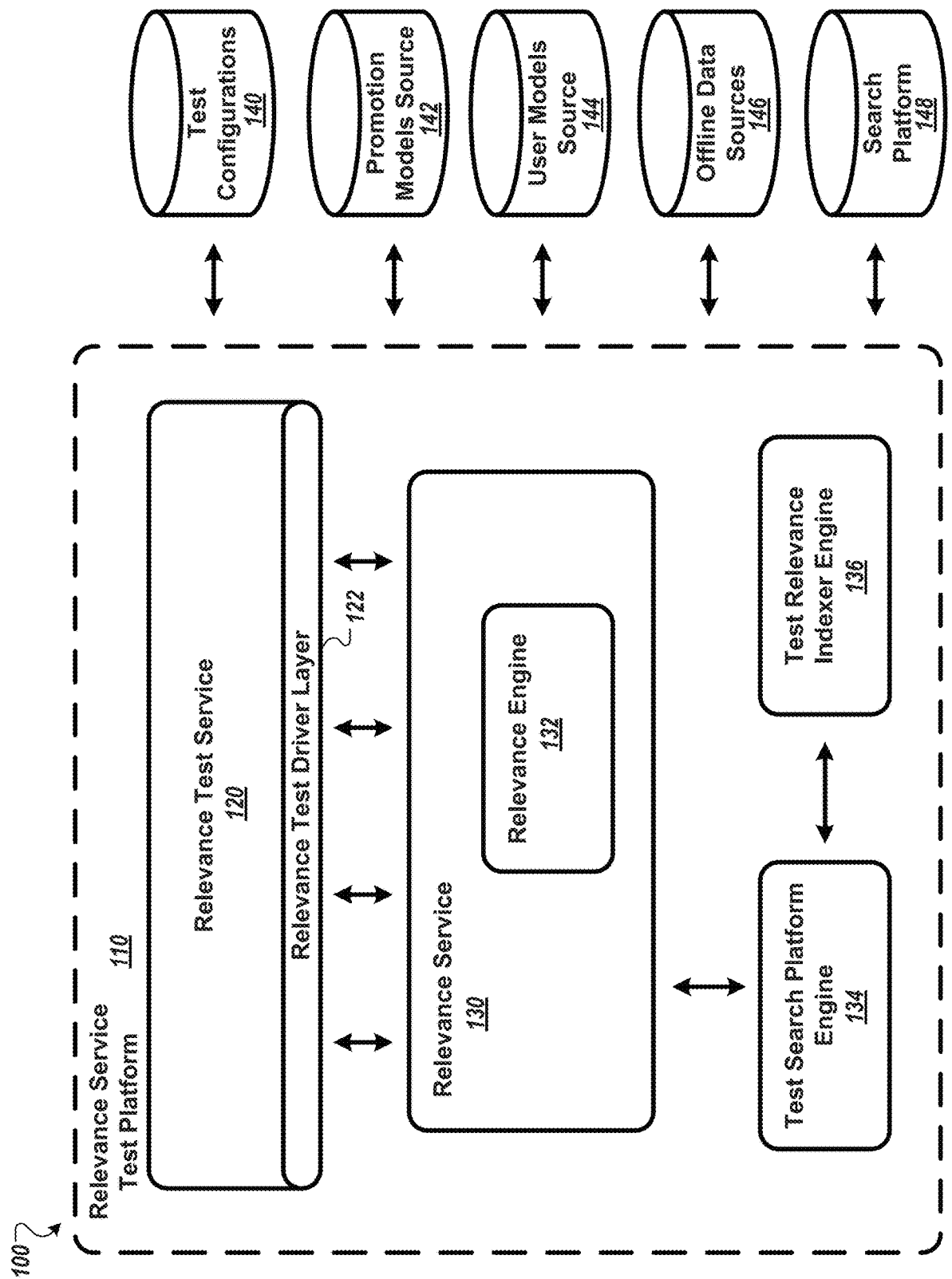
Figure 3:
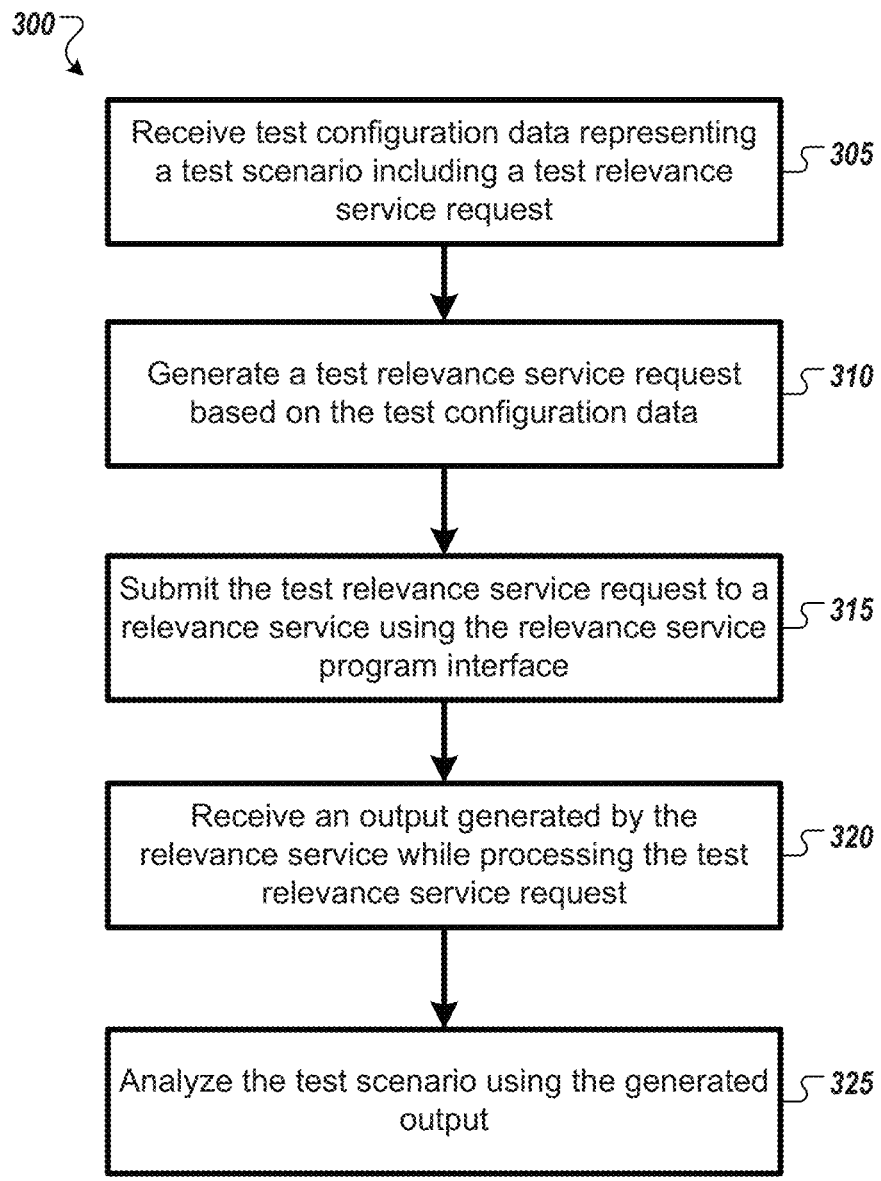
Figure 6:
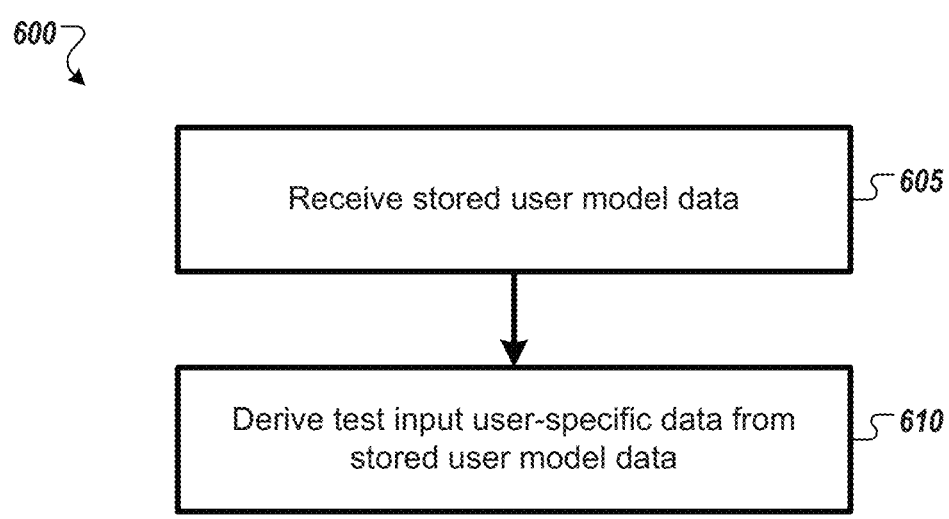
Figure 9:
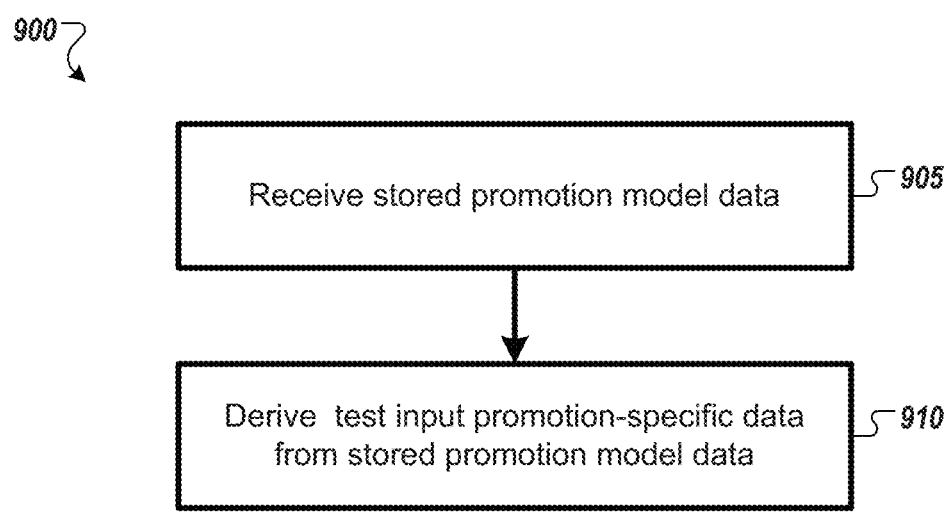
Figure 10:
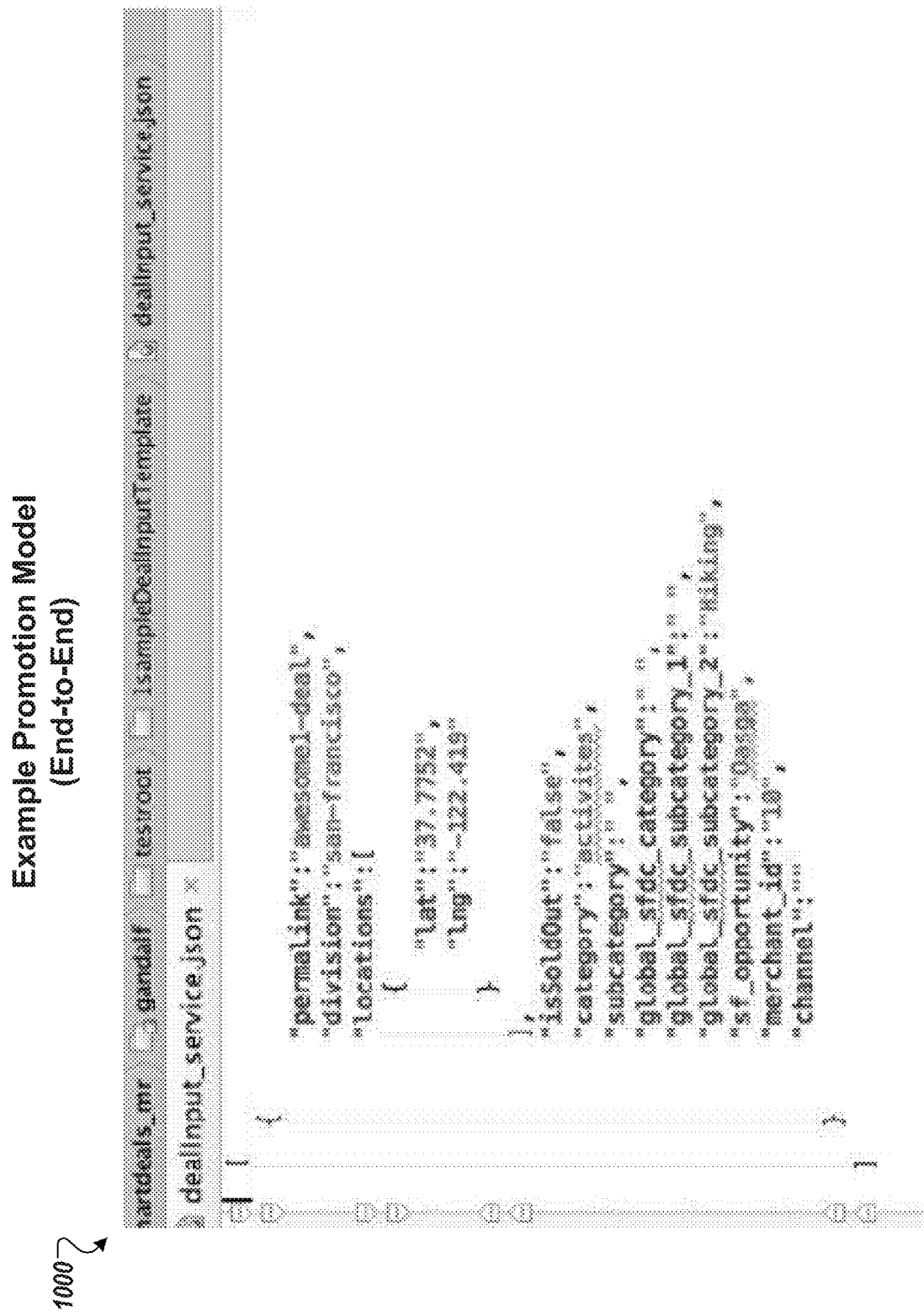
Figure 13:
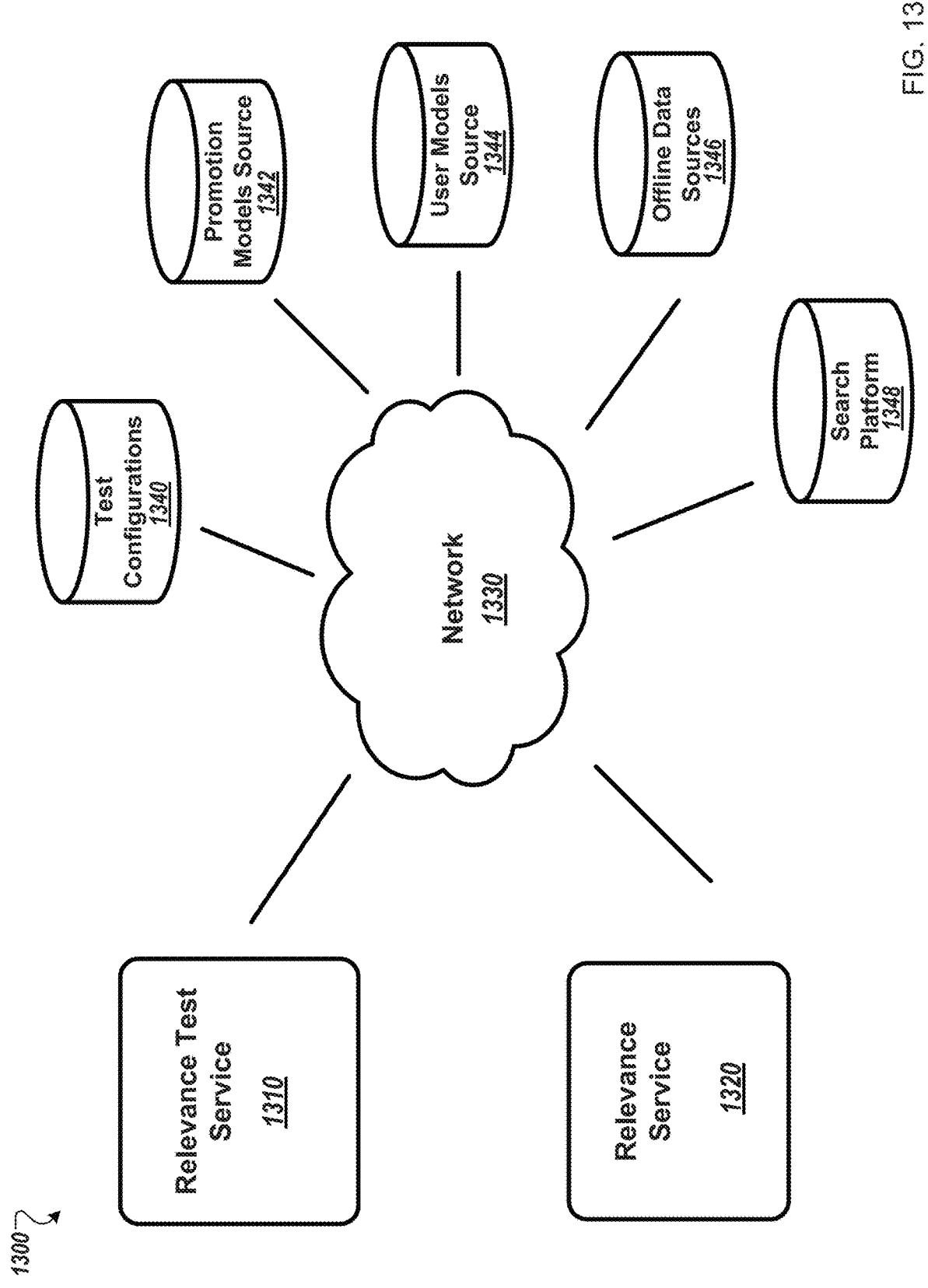
Figure 14:
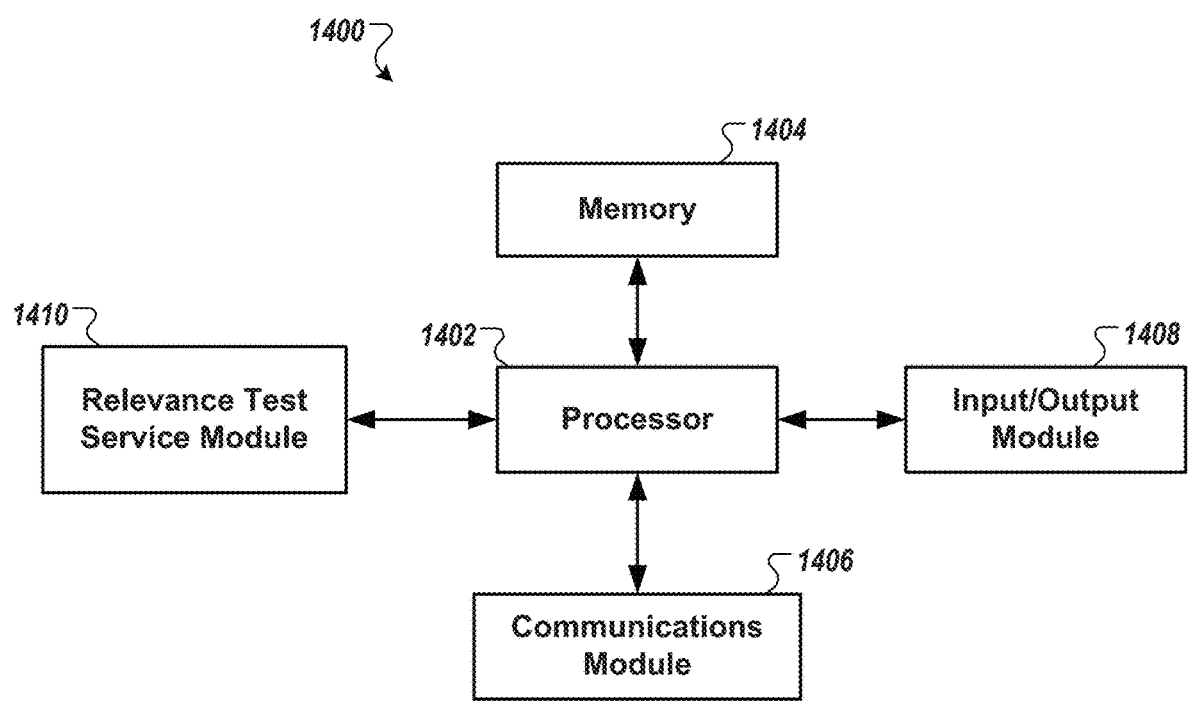

Having thus described the invention in general terms, reference will now be made to the accompanying drawings, which are not necessarily drawn to scale, and wherein:

FIG. 1 illustrates an example system that can be configured to implement verification and validation of a relevance service in accordance with some embodiments discussed herein;

FIG. 2 illustrates an example of a test configuration representing an end-to-end test scenario in accordance with some embodiments discussed herein;

FIG. 3 is a flow diagram of an example method 300 for verifying and/or validating a relevance service in accordance with some embodiments discussed herein;

FIG. 4 illustrates an example of JSON configuration data representing input parameters in accordance with some embodiments discussed herein;

FIG. 5 illustrates an example 500 of JSON configuration data representing the expected output data from the relevance service while processing a test scenario in accordance with some embodiments discussed herein;

FIG. 6 is a flow diagram of an example method for generating user-specific input data to be used in a test scenario in accordance with some embodiments discussed herein;

Figure 7:
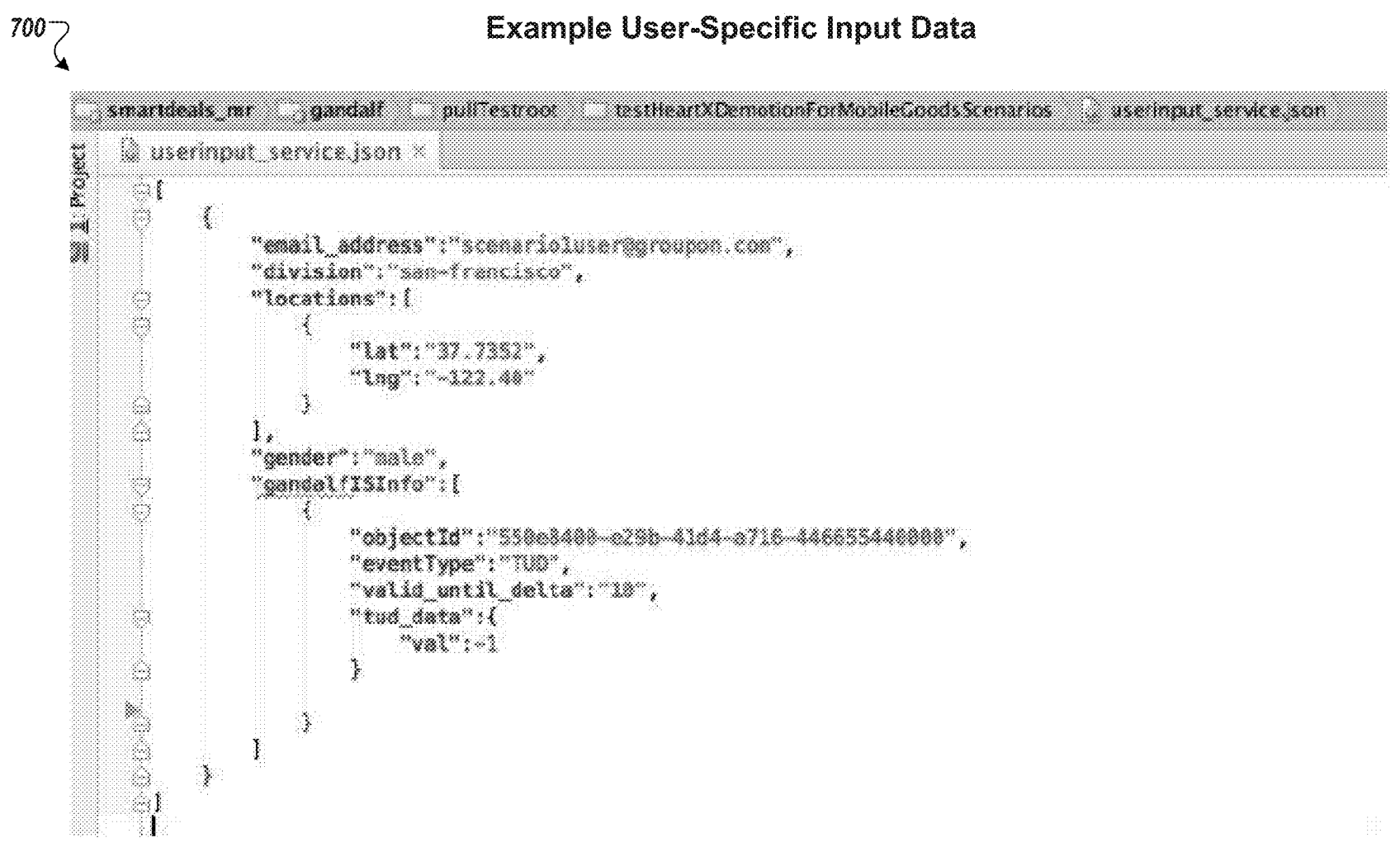

FIG. 7 illustrates an example of JSON configuration data representing user-specific input parameters in accordance with some embodiments discussed herein;

Figure 8:
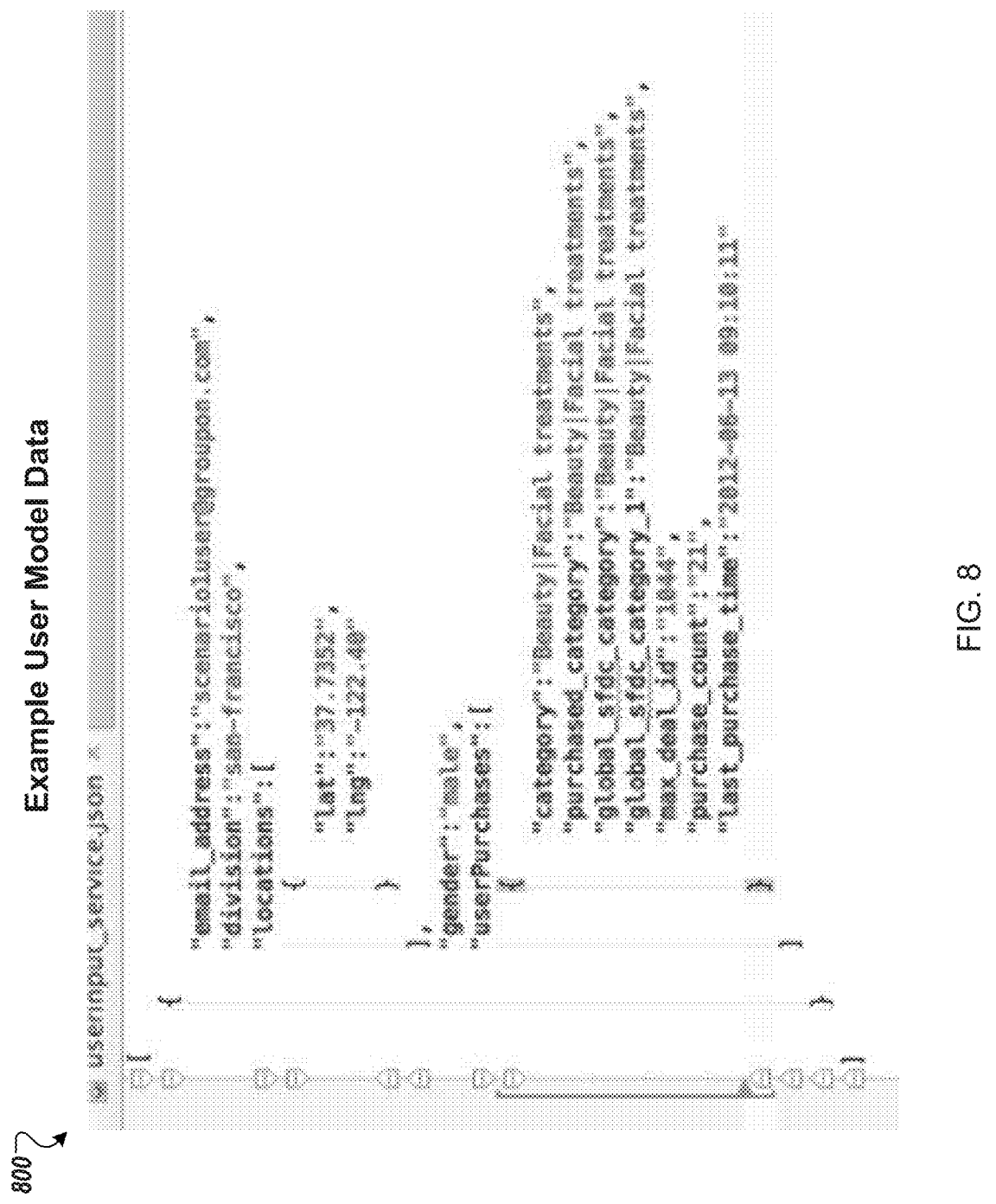

FIG. 8 illustrates an example of JSON configuration data representing user-specific attributes that include the user's previous consumer behavior including past purchases and access status of promotions in accordance with some embodiments discussed herein;

FIG. 9 is a flow diagram of an example method for generating promotion-specific input data to be used in a test scenario in accordance with some embodiments discussed herein;

FIG. 10 illustrates an example of JSON configuration data representing promotion-specific input data that are included in test configuration data describing an end-to-end test scenario in accordance with some embodiments discussed herein;

FIG. 11 illustrates an example of JSON configuration data representing promotion-specific input data including attributes that describe promotion performance in accordance with some embodiments discussed herein;

FIG. 12 illustrates an example of JSON configuration data representing promotion-specific input data that include mock search input data in accordance with some embodiments discussed herein;

FIG. 13 illustrates an example network architecture for a relevance service test platform in accordance with some embodiments discussed herein; and FIG. 14 illustrates a schematic block diagram of circuitry that can be included in a computing device, such as a relevance test service module, in accordance with some embodiments discussed herein.

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

As used herein, the terms "data," "content," "information" and similar terms may be used interchangeably to refer to data capable of being captured, transmitted, received, displayed and/or stored in accordance with various example embodiments. Thus, use of any such terms should not be taken to limit the spirit and scope of the disclosure. Further, where a computing device is described herein to receive data from another computing device, the data may be received directly from the another computing device or may be received indirectly via one or more intermediary computing devices, such as, for example, one or more servers, relays, routers, network access points, base stations, and/or the like. Similarly, where a computing device is described herein to send data to another computing device, the data may be sent directly to the another computing device or may be sent indirectly via one or more intermediary computing devices, such as, for example, one or more servers, relays, routers, network access points, base stations, and/or the like.

In embodiments, a relevance service may identify promotions available to a user by using attributes of promotions that are stored in a promotions repository and/or attributes of user profile data representing the user. The relevance service may then process that set of promotions for relevance based on a filtering workflow, which is a combination of filtering algorithms and rules that are applied in sequence to further prune the initially identified set of promotions.

In embodiments, the relevance service may weight each identified promotion based its relevance to the user, and then rank the set of identified available promotions based on their respective weights as described, for example, in U.S. patent application Ser. No. 13/829,581 entitled "Promotion Offering System" and filed on Mar. 14, 2013, which is incorporated herein in its entirety.

As such, and according to some example embodiments, the systems and methods described herein are therefore configured to provide a configurable test environment within which a relevance service can be invoked to execute one or a combination of test scenarios, each test scenario respectively being configured to exercise one or a combination of features of the relevance service.

In embodiments, a test scenario may be configured to use test data derived from one or a combination of user models and promotion models based on aggregated data that has been collected from previous production runs of the relevance service. In embodiments, each test scenario is described as a set of test configuration data.

Examples of test scenarios that may be executed in the test environment include end-to-end test scenarios (i.e., use all relevance service components in sequence) and directed test scenarios (i.e., use only specified relevance service components) for verification and validation of filtering algorithms and/or algorithm parity; verification of business rules used in filters, and validation of search results and search quality. In embodiments, a test scenario can be based on mock data (e.g., modeled data and/or data collected from previous production runs of the relevance service). Additionally and/or alternatively, in embodiments, simulation test scenarios using data describing new promotions enable use of the test environment as a production monitor for verification and validation of the new promotion data before their release.

FIG. 1 illustrates an example system 100 that can be configured to implement verification and validation of a relevance service. System 100 comprises a relevance service test platform 110 that includes a relevance test service 120, a test search platform engine 134, and a test relevance indexer engine 136. The relevance test service 120 is configured to include a relevance test driver layer 122 that interfaces to at least one application programming interface (API) presented by at least one component of the relevance service 130. In embodiments, the relevance service 130 includes a relevance engine 132.

The components of system 100 can be communicatively coupled to one or more of each other. Though the components identified above are described as being separate or distinct, two or more of the components may be combined into a single process or routine. The functional description provided herein including separation of responsibility for distinct functions is by way of example. Other groupings or other divisions of functional responsibilities can be made as necessary or in accordance with design preferences. System 100 further includes communicative coupling of one or more system components to a test configuration repository 140, a promotion models source repository 142, a user models source repository 144, an offline data sources repository 146, and a search platform data repository 148.

In embodiments, relevance service 130 may be associated with a promotions provider, and be configured to execute a relevance service request on behalf of a user to identify one or more available promotions that are relevant to the user. For example, a relevance service request may be generated in response to the user interacting with a page from a web site that is published by the promotions provider. In another example, the relevance service request may be generated by a search service during processing of a search query from a user for promotions having particular attributes (e.g., a promotions search query for family-friendly restaurants located in San Francisco, California).

In embodiments, a relevance engine 132 may process a relevance request on behalf of a user by initially identifying the set of all promotions potentially available to the user and then processing that set of promotions for relevance based on a filtering workflow, which is a combination of filtering algorithms and rules that are applied in sequence to further prune the initially identified set of promotions.

In embodiments, at least one global filtering algorithm may be the basis for the initial selection criteria to identify the set of potentially available promotions. Examples of initial selection criteria include location attributes (e.g., only selecting promotions having locations within 25 miles of San Francisco) and promotion sold-out status (e.g., not selecting any promotion associated with a status attribute value of "sold out").

In embodiments, relevance engine 132 dispatches the identified set of all potentially available promotions to a filtering workflow for further processing. In embodiments, the selection of the filtering workflow to use for processing of a relevance request may be based on one or a combination of several criteria. In some embodiments, for example, the selection of a filtering workflow to use for processing a request is based on a hashing function applied to at least one user attribute and/or one or a combination of attributes associated with the user that is associated with the request (e.g., user's current location); associated with the request (e.g., current time of day); and/or associated with the type of request (e.g., a search request). Additionally or alternatively, in some embodiments, the selection of the filtering workflow to which a request is dispatched is based on aggregated promotion performance data that has been collected from the results of previously processed user requests (e.g., a current user request may be dispatched to a filtering workflow that is associated with identifying promotions that, based on previous consumer behavior, have a high likelihood of being purchased by the user).

In embodiments, relevance engine 132 executes a relevance request received from a search platform by returning search results that are ranked in terms of the relevance of the promotions represented in the results. In embodiments, relevance service 130 receives test search result promotion data that match the search terms in a test search query from test search platform engine 134. The test search result promotion data are received from test relevance indexer engine 136, which retrieves the data from one or more data repositories specified in a test configuration, e.g., promotions models source repository 142 and offline data sources 146.

In embodiments, relevance service test platform 110 provides a configurable test environment within which the relevance service 130 can be invoked to execute one or a combination of test scenarios, each test scenario respectively being configured to exercise one or a combination of features of the relevance service 130. In embodiments, a test scenario may be configured to use test data derived from one or a combination of user models and promotion models based on aggregated data that has been collected from previous production runs of the relevance service 130. In embodiments, stored data representing promotion models, user models, and previously collected data from production runs are accessed by the relevance service test platform 110 from a promotion models source repository 142, a user models source repository 144, and an offline data sources repository 146, respectively. In embodiments, each test scenario is described as a set of test configuration data. In some embodiments, the test configuration data are represented in a data interchange format that is both human and machine-readable, e.g., JavaScript Object Notation (JSON). In embodiments, test configuration data is stored in a test configurations repository 140 that is accessed by the relevance service test platform 110.

In embodiments, test configuration data may describe one of several types of test scenario. For example, a test configuration may describe an end-to-end test scenario in which the relevance service 130 processes all components of a relevance service task in response to receiving a test relevance service request. Alternatively, in some embodiments, a test configuration may describe a directed test scenario that exercises one or a combination of relevance service processing components, e.g., the scenario specifies processing the test relevance service request only using a specified set of filtering workflows.

In some embodiments, a test configuration may describe a mock test scenario based on test input data that is simulated and/or is derived from one or a combination of user models and promotion models, and/or be based on aggregated data that has been collected from previous production runs of the relevance service 130. Thus, a mock test scenario can be generated to test and/or verify the performance of particular system components and/or be used to verify aspects of models that are deployed or planned for deployment in the production system. For example, the input data for a particular scenario may represent a search for promotions from pizza restaurants within proximity of Mountain View, California. In embodiments, a mock test scenario representing a search for promotions from pizza restaurants within proximity of another location, e.g., San Francisco, California, can be derived from the particular scenario by modifying the location specified in the test input data.

FIG. 2 illustrates an example of a test configuration 200 representing an end-to-end test scenario. The test configuration 200 is represented as a set of component configuration data JSON files that include the input parameters 210 to be used in generating the test relevance service request, data representing attributes of a model user 220 on behalf of whom the test relevance service request was submitted, data representing the attributes of a set of model promotions ("deals" in this example) 230 potentially available to the model user, and output data 240 expected to be returned from the relevance service 130 as a result of processing the test relevance service request. The components of the example test configuration 200 will be described in more detail below with respect to method 300.

FIG. 3 is a flow diagram of an example method 300 for verifying and/or validating a relevance service. For convenience, the method 300 will be described with respect to a system that includes one or more computing devices and performs the method 300. Specifically, the method 300 will be described with respect to the relevance service test platform 110 of system 100 and, more specifically, with respect to the relevance test service 120.

In embodiments, the system receives 305 a test configuration representing a test case scenario, e.g., the example test configuration 200.

In embodiments, the system generates 310 a test relevance service request based on the test configuration data. The test relevance service request may be generated as a Universal Resource Locator (URL), representing a request that would be generated at a website page in response to a user's interaction with that page. Alternatively, the test relevance service request may be generated as a search request, representing a request generated by a search platform 148 in response to the search platform 148 receiving a search query from a user.

In some embodiments, the relevance test service 120 includes a relevance test driver layer 122, and the test relevance service request is submitted 315 as an invocation of the service request API of the relevance service 130 by a relevance test driver. Directly invoking the relevance service request API facilitates more accurate testing of the relevance service 130, and also enables the relevance test service 120 to be modified and scale gracefully as the relevance service 130 design evolves.

In embodiments, the system receives 320 output data generated from the relevance service 130 as a result of processing the test relevance service request. In some embodiments, the output data generated by the relevance service 130 include a list of promotions that are ranked based on their relevance to the user associated with the relevance service request.

In embodiments, the system analyzes 325 the test scenario based on the received output data. In some embodiments, the analysis includes comparing the received output data to the expected output data 240 specified in the test configuration. The results of the analysis are used for verification and validation of the performance of the relevance system.

In some embodiments, relevance service test platform 110 is configured to support a flexible reporting model that enables generation of one or a combination of several types of reports of test output and/or analysis. In embodiments, relevance service test platform 110 may include a reporting framework that supports generating a test report in any or all of a variety of reporting formats (e.g., HTML, graphs, and email) and, additionally or alternatively, generating a test report that can be shared among a group of collaborators.

FIG. 4 illustrates an example 400 of JSON configuration data representing the input parameters 210 of test configuration 200. In this example, the input parameters represent parameters of an HTTP request to the relevance service from a model user, and specify data including the user's email address ("scenario1user@groupon.com"), division ("san-francisco"), and request date ("2012-04-25"). In embodiments, the input parameters also may include the relevance service API to be called when the request is invoked as well as a request context ("default" in this example) and other flags for specifying the processing of the test relevance service request by the relevance service 130.

In embodiments, the input parameters of a test configuration may include configurable flags that specify the type of processing that the relevance service 130 will apply when processing the test relevance service request. For example, in some embodiments, the input parameters may include a configurable blacklist flag that specifies one or more filtering workflows that are not to be included in the processing of the test relevance service request. Turning to the example input parameters 400, "exclude_ranking_groups" is a flag that specifies a list of filtering workflows that are not to be applied by the relevance service 130 during the processing of the test relevance service request that is specified by the input parameters 400.

In embodiments, a filtering workflow and/or at least one filter within a workflow may be associated with one or more configurable flags that modify processing using the filtering workflow. In some embodiments, each configurable flag has an activation status, and the flag may be configured by setting of the flag's activation status. Additionally and/or alternatively, in some embodiments, an additional configurable flag may be associated with a filtering workflow or a filter during execution of a test scenario.

FIG. 5 illustrates an example 500 of JSON configuration data representing the expected output data 240 to be generated by the relevance service 130 while processing the test scenario represented by test configuration 200. The expected output data include a ranked list of promotions (i.e., "deals"), each promotion being represented by a permalink, and also being associated with a category and with one or more locations. The expected output data also include a user key 504, a context 506, and the set of filtering workflows (i.e., the treatment 508) that was applied by the relevance service when processing the test relevance service request.

In some embodiments, a relevance service 130 is configured to include multiple treatments that potentially could be applied, and the relevance service 130 determines which treatment to use in processing a relevance service request at the time the request is received. For example, in some embodiments, the selection of a treatment to apply for a submitted relevance service request is based on one or a combination of selection criteria. In embodiments, the selection of a treatment may include, for example, determining a treatment that matches the result of applying a hash function to at least one attribute (e.g., a user identifier) of the user on behalf of whom the relevance service request to be processed was submitted, determining a treatment that has been assigned to the majority of recently received user requests, determining a treatment that was recently added to the configuration, and/or identifying the treatment that, as a result of A/B testing against another of the multiple treatments, was determined to result in the most successful outcomes (e.g., promotion purchases) based on an analysis of consumer response to the returned promotions from the two treatments being tested.

FIG. 6 is a flow diagram of an example method 600 for generating user-specific input data to be used in a test scenario. For convenience, the method 600 will be described with respect to a system that includes one or more computing devices and performs the method 600. Specifically, the method 600 will be described with respect to the relevance service test platform 110 of system 100 and, more specifically, with respect to the relevance test service 120.

In embodiments, the system retrieves 605 stored data representing at least one user model, and then derives 610 user-specific input parameters based on the user model data.

In embodiments, the system derives user-specific attribute data based on data representing at least one user model. The user model data is used to create user-specific attribute data such as email address, location, gender, and data describing user personalization attributes such as themes and preferences. In some embodiments data representing user models is stored in a user models source repository 144.

FIG. 7 illustrates an example 700 of JSON configuration data representing user-specific input parameters 220 that are included in the example test configuration 200. The user-specific input parameters include attributes of the user (e.g., gender) as well as attributes of the request associated with the user (e.g., eventType and valid_until_delta).

FIG. 8 illustrates an example 800 of JSON configuration data representing user-specific attributes that include the user's previous consumer behavior including past purchases and access status of promotions (e.g., "userPurchases"). In embodiments, collected and aggregated data representing previous consumer behavior are stored in an offline data sources repository, and the system may derive at least some of the user-specific attribute data based on stored data retrieved from the offline data sources repository.

FIG. 9 is a flow diagram of an example method 900 for generating promotion-specific input data to be used in a test scenario. For convenience, the method 900 will be described with respect to a system that includes one or more computing devices and performs the method 900. Specifically, the method 900 will be described with respect to the relevance service test platform 110 of system 100 and, more specifically, with respect to the relevance test service 120.

In embodiments, the system retrieves 905 stored data representing a set of promotion attributes, and then derives 910 promotion-specific input data based on the promotion model data. In embodiments, promotion-specific input data may represent one or a combination of attributes including promotion permalink, promotion type, an identifier of the merchant associated with the promotion, promotion category and/or subcategory, locations at which the promotion is run, and sold-out status of the promotion.

FIG. 10 illustrates an example 1000 of JSON configuration data representing promotion-specific input data 230 that are included in the test configuration 200. Test configuration 200 is an example of a description of an end-to-end test scenario. In embodiments, the promotion-specific input data are the basis for the selection criteria used by the relevance service 130 in the initial selection of promotions that are available to the model user.

FIG. 11 illustrates an example 1100 of JSON configuration data representing promotion-specific input data including attributes that describe promotion performance (e.g., "deal_performance_data"). In embodiments, collected and aggregated data representing promotion performance are stored in an offline data sources repository, and the system may derive at least some of the promotion-specific attribute data based on stored data retrieved from the offline data sources repository.

FIG. 12 illustrates an example 1200 of JSON configuration data representing promotion-specific input data that include mock search input data. As previously described with respect to system 100, a relevance service may receive a relevance service request from a search platform 148.

As previously described with respect to method 300, test configuration data may describe a search relevance test scenario. As illustrated in example 1200, the promotion attributes represented in the promotion-specific input data additionally include mock search input data that would have been extracted from the search platform 148.

In some embodiments, relevance service test platform 110 is configured to support delta-based model generation for test configurations. In delta-based model generation, an existing user and/or promotion model can be used as a template for generating a new user and/or promotion model. Thus, instead of building the new model from scratch, the new model can be generated by incrementally modifying one or a combination of parameters in the existing model template.

FIG. 13 illustrates example network architecture 1300 for a relevance service test platform, which may include one or more devices and sub-systems that are configured to implement some embodiments discussed herein. For example, system 1300 may include relevance test service 1310, relevance service 1320, test configurations repository 1340, promotion models source repository 1342, user models source repository 1344, offline data sources repository 1346, and search platform 1348. Relevance test service 1310 can include, for example, a relevance test driver layer (not shown). Relevance service 1320 can include, for example, relevance engine, search platform engine, and relevance indexer engine (not shown). Relevance test service 1310 and relevance service 1320 each respectively can be any suitable network server and/or other type of processing device. Test configurations repository 1340, promotion models source repository 1342, user models source repository 1344, offline data sources repository 1346, and search platform 1348 each respectively can be any suitable network database configured to store data, such as that discussed herein. In this regard relevance service test platform 1300 may include, for example, at least one backend data server, network database, and/or cloud computing device, among other things.

FIG. 14 shows a schematic block diagram of circuitry 1400, some or all of which may be included in, for example, relevance service test platform 1300. As illustrated in FIG. 14, in accordance with some example embodiments, circuitry 1400 can include various means, such as processor 1402, memory 1404, communications module 1406, and/or input/output module 1408. As referred to herein, "module" includes hardware, software and/or firmware configured to perform one or more particular functions. In this regard, the means of circuitry 1400 as described herein may be embodied as, for example, circuitry, hardware elements (e.g., a suitably programmed processor, combinational logic circuit, and/or the like), a computer program product comprising computer-readable program instructions stored on a non-transitory computer-readable medium (e.g., memory 1404) that is executable by a suitably configured processing device (e.g., processor 1402), or some combination thereof.

Processor 1402 may, for example, be embodied as various means including one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits such as, for example, an ASIC (application specific integrated circuit) or FPGA (field programmable gate array), or some combination thereof. Accordingly, although illustrated in FIG. 14 as a single processor, in some embodiments, processor 1402 comprises a plurality of processors. The plurality of processors may be embodied on a single computing device or may be distributed across a plurality of computing devices collectively configured to function as circuitry 1400. The plurality of processors may be in operative communication with each other and may be collectively configured to perform one or more functionalities of circuitry 1400 as described herein. In an example embodiment, processor 1402 is configured to execute instructions stored in memory 1404 or otherwise accessible to processor 1402. These instructions, when executed by processor 1402, may cause circuitry 1400 to perform one or more of the functionalities of circuitry 1400 as described herein.

Whether configured by hardware, firmware/software methods, or by a combination thereof, processor 1402 may comprise an entity capable of performing operations according to embodiments of the present invention while configured accordingly. Thus, for example, when processor 1402 is embodied as an ASIC, FPGA or the like, processor 1402 may comprise specifically configured hardware for conducting one or more operations described herein. Alternatively, as another example, when processor 1402 is embodied as an executor of instructions, such as may be stored in memory 1404, the instructions may specifically configure processor 1402 to perform one or more algorithms and operations described herein, such as those discussed in connection with FIGS. 3, 6, and 9.

Memory 1404 may comprise, for example, volatile memory, non-volatile memory, or some combination thereof. Although illustrated in FIG. 14 as a single memory, memory 1404 may comprise a plurality of memory components. The plurality of memory components may be embodied on a single computing device or distributed across a plurality of computing devices. In various embodiments, memory 1404 may comprise, for example, a hard disk, random access memory, cache memory, flash memory, a compact disc read only memory (CD-ROM), digital versatile disc read only memory (DVD-ROM), an optical disc, circuitry configured to store information, or some combination thereof. Memory 1404 may be configured to store information, data (including analytics data), applications, instructions, or the like for enabling circuitry 1400 to carry out various functions in accordance with example embodiments of the present invention. For example, in at least some embodiments, memory 1404 is configured to buffer input data for processing by processor 1402. Additionally or alternatively, in at least some embodiments, memory 1404 is configured to store program instructions for execution by processor 1402. Memory 1404 may store information in the form of static and/or dynamic information. This stored information may be stored and/or used by circuitry 1400 during the course of performing its functionalities.

Communications module 1406 may be embodied as any device or means embodied in circuitry, hardware, a computer program product comprising computer readable program instructions stored on a computer readable medium (e.g., memory 1404) and executed by a processing device (e.g., processor 1402), or a combination thereof that is configured to receive and/or transmit data from/to another device, such as, for example, a second circuitry 1400 and/or the like. In some embodiments, communications module 1406 (like other components discussed herein) can be at least partially embodied as or otherwise controlled by processor 1402. In this regard, communications module 1406 may be in communication with processor 1402, such as via a bus. Communications module 1406 may include, for example, an antenna, a transmitter, a receiver, a transceiver, network interface card and/or supporting hardware and/or firmware/software for enabling communications with another computing device. Communications module 1406 may be configured to receive and/or transmit any data that may be stored by memory 1404 using any protocol that may be used for communications between computing devices. Communications module 1406 may additionally or alternatively be in communication with the memory 1404, input/output module 1408 and/or any other component of circuitry 1400, such as via a bus.

Input/output module 1408 may be in communication with processor 1402 to receive an indication of a user input and/or to provide an audible, visual, mechanical, or other output to a user. Some example visual outputs that may be provided to a user by circuitry 1400 are discussed in connection with FIG. 1. As such, input/output module 1408 may include support, for example, for a keyboard, a mouse, a joystick, a display, a touch screen display, a microphone, a speaker, a RFID reader, barcode reader, biometric scanner, and/or other input/output mechanisms. In embodiments wherein circuitry 1400 is embodied as a server or database, aspects of input/output module 1408 may be reduced as compared to embodiments where circuitry 1400 is implemented as an end-user machine or other type of device designed for complex user interactions. In some embodiments (like other components discussed herein), input/output module 1408 may even be eliminated from circuitry 1400. Alternatively, such as in embodiments wherein circuitry 1400 is embodied as a server or database, at least some aspects of input/output module 1408 may be embodied on an apparatus used by a user that is in communication with circuitry 1400, such as for example, pharmacy terminal 108. Input/output module 1408 may be in communication with the memory 1404, communications module 1406, and/or any other component(s), such as via a bus. Although more than one input/output module and/or other component can be included in circuitry 1400, only one is shown in FIG. 14 to avoid overcomplicating the drawing (like the other components discussed herein).

Relevance test service module 1410 may also or instead be included and configured to perform the functionality discussed herein related to the verification and validation of a relevance service discussed above. In some embodiments, some or all of the functionality of verification and validation may be performed by processor 1402. In this regard, the example processes and algorithms discussed herein can be performed by at least one processor 1402 and/or relevance test service module 1410. For example, non-transitory computer readable media can be configured to store firmware, one or more application programs, and/or other software, which include instructions and other computer-readable program code portions that can be executed to control each processor (e.g., processor 1402 and/or relevance test service module 1410) of the components of system 400 to implement various operations, including the examples shown above. As such, a series of computer-readable program code portions are embodied in one or more computer program products and can be used, with a computing device, server, and/or other programmable apparatus, to produce machine-implemented processes.

Any such computer program instructions and/or other type of code may be loaded onto a computer, processor or other programmable apparatus's circuitry to produce a machine, such that the computer, processor other programmable circuitry that execute the code on the machine create the means for implementing various functions, including those described herein.

It is also noted that all or some of the information presented by the example displays discussed herein can be based on data that is received, generated and/or maintained by one or more components of system 1300. In some embodiments, one or more external systems (such as a remote cloud computing and/or data storage system) may also be leveraged to provide at least some of the functionality discussed herein.

As described above, aspects of embodiments of the present invention may be configured as methods, mobile devices, backend network devices, and the like. Accordingly, embodiments may comprise various means including entirely of hardware or any combination of software and hardware. Furthermore, embodiments may take the form of a computer program product on at least one non-transitory computer-readable storage medium having computer-readable program instructions (e.g., computer software) embodied in the storage medium. Any suitable computer-readable storage medium may be utilized including non-transitory hard disks, CD-ROMs, flash memory, optical storage devices, or magnetic storage devices.

Embodiments of the present invention have been described above with reference to block diagrams and flowchart illustrations of methods, apparatuses, systems and computer program products. It will be understood that each block of the circuit diagrams and process flow diagrams, and combinations of blocks in the circuit diagrams and process flowcharts, respectively, can be implemented by various means including computer program instructions. These computer program instructions may be loaded onto a general purpose computer, special purpose computer, or other programmable data processing apparatus, such as processor 1402 and/or relevance test service module 1410 discussed above with reference to FIG. 14, to produce a machine, such that the computer program product includes the instructions which execute on the computer or other programmable data processing apparatus create a means for implementing the functions specified in the flowchart block or blocks.

These computer program instructions may also be stored in a computer-readable storage device (e.g., memory 1404) that can direct a computer or other programmable data processing apparatus to function in a particular manner, such that the instructions stored in the computer-readable storage device produce an article of manufacture including computer-readable instructions for implementing the function discussed herein. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions discussed herein.

Accordingly, blocks of the block diagrams and flowchart illustrations support combinations of means for performing the specified functions, combinations of steps for performing the specified functions and program instruction means for performing the specified functions. It will also be understood that each block of the circuit diagrams and process flowcharts, and combinations of blocks in the circuit diagrams and process flowcharts, can be implemented by special purpose hardware-based computer systems that perform the specified functions or steps, or combinations of special purpose hardware and computer instructions Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A relevance service comprising one or more computers and one or more storage devices storing instructions that are operable, when executed by the one or more computers, to cause the one or more computers to:
   receive, via at least one relevance test driver that interfaces with a relevance test service, test configuration data associated with at least one test scenario for the relevance service;
   determine one or more promotions relevant to a user identifier based at least in part on the test configuration data; and
   transmit output data associated with the one or more promotions to the relevance test service.

2. The relevance service of claim 1, wherein the one or more storage devices store instructions that are operable, when executed by the one or more computers, to further cause the one or more computers to:
   receive, via the at least one relevance test driver, model data related to one or more models; and
   determine the one or more promotions based at least in part on the model data.

3. The relevance service of claim 1, wherein the one or more storage devices store instructions that are operable, when executed by the one or more computers, to further cause the one or more computers to:
   receive, via the at least one relevance test driver, user attribute data related to the user identifier; and
   determine the one or more promotions based at least in part on the user attribute data.

4. The relevance service of claim 1, wherein the one or more storage devices store instructions that are operable, when executed by the one or more computers, to further cause the one or more computers to:
   receive, via the at least one relevance test driver, promotion attribute data related to a set of promotions; and
   determine the one or more promotions based at least in part on the promotion attribute data.

5. The relevance service of claim 1, wherein the one or more storage devices store instructions that are operable, when executed by the one or more computers, to further cause the one or more computers to:
   receive, via the at least one relevance test driver, historical test configuration data related to at least one historical test scenario; and
   determine the one or more promotions based at least in part on the historical test configuration data.

6. The relevance service of claim 1, wherein the one or more storage devices store instructions that are operable, when executed by the one or more computers, to further cause the one or more computers to:
   receive the test configuration data as one or more data interchange format data objects via the at least one relevance test driver.

7. The relevance service of claim 1, wherein the one or more storage devices store instructions that are operable, when executed by the one or more computers, to further cause the one or more computers to:
   receive the test configuration data via at least one application programming interface associated with the at least one relevance test driver.

8. A computer-implemented method, comprising:
   receiving, by a computing device comprising a processor, test configuration data associated with at least one test scenario for a relevance service via at least one relevance test driver that interfaces with a relevance test service;
   determining, by the computing device, one or more promotions relevant to a user identifier based at least in part on the test configuration data; and
   transmitting, by the computing device, output data associated with the one or more promotions to the relevance test service.

9. The computer-implemented method of claim 8, further comprising:
   receiving, by the computing device, model data related to one or more models via the at least one relevance test driver; and
   determining, by the computing device, the one or more promotions based at least in part on the model data.

10. The computer-implemented method of claim 8, further comprising:
    receiving, by the computing device, user attribute data related to the user identifier via the at least one relevance test driver; and
    determining, by the computing device, the one or more promotions based at least in part on the user attribute data.

11. The computer-implemented method of claim 8, further comprising:
    receiving, by the computing device, promotion attribute data related to a set of promotions via the at least one relevance test driver; and
    determining, by the computing device, the one or more promotions based at least in part on the promotion attribute data.

12. The computer-implemented method of claim 8, further comprising:
    receiving, by the computing device, historical test configuration data related to at least one historical test scenario via the at least one relevance test driver; and
    determining, by the computing device, the one or more promotions based at least in part on the historical test configuration data.

13. The computer-implemented method of claim 8, further comprising:
    receiving, by the computing device, the test configuration data as one or more data interchange format data objects via the at least one relevance test driver.

14. The computer-implemented method of claim 8, further comprising:
receiving, by the computing device, the test configuration data via at least one application programming interface associated with the at least one relevance test driver.

15. A computer program product, stored on a computer readable medium, comprising instructions that when executed by one or more computers cause the one or more computers to:
receive, via at least one relevance test driver that interfaces with a relevance test service, test configuration data associated with at least one test scenario for a relevance service;
determine one or more promotions relevant to a user identifier based at least in part on the test configuration data; and
transmit output data associated with the one or more promotions to the relevance test service.

16. The computer program product of claim 15, further comprising instructions that when executed by the one or more computers cause the one or more computers to:
receive, via the at least one relevance test driver, model data related to one or more models; and
determine the one or more promotions based at least in part on the model data.

17. The computer program product of claim 15, further comprising instructions that when executed by the one or more computers cause the one or more computers to:
receive, via the at least one relevance test driver, user attribute data related to the user identifier; and
determine the one or more promotions based at least in part on the user attribute data.

18. The computer program product of claim 15, further comprising instructions that when executed by the one or more computers cause the one or more computers to:
receive, via the at least one relevance test driver, promotion attribute data related to a set of promotions; and
determine the one or more promotions based at least in part on the promotion attribute data.

19. The computer program product of claim 15, further comprising instructions that when executed by the one or more computers cause the one or more computers to:
receive, via the at least one relevance test driver, historical test configuration data related to at least one historical test scenario; and
determine the one or more promotions based at least in part on the historical test configuration data.

20. The computer program product of claim 15, further comprising instructions that when executed by the one or more computers cause the one or more computers to:
receive the test configuration data as one or more data interchange format data objects via the at least one relevance test driver.

* * * * *